US005506250A

United States Patent [19]
Gouot et al.

[11] Patent Number: 5,506,250
[45] Date of Patent: Apr. 9, 1996

[54] METHOD OF TREATING TURF

[75] Inventors: Jean M. Gouot, Au Mont D'or; Maurice Chazalet, Anse, both of France; Mark White, Landisville, Pa.

[73] Assignee: Rhone-Poulenc Inc., Research Triangle Park, N.C.

[21] Appl. No.: 339,676

[22] Filed: Nov. 14, 1994

[51] Int. Cl.$^6$ ............................................. A01N 43/64
[52] U.S. Cl. ............................................. 514/383
[58] Field of Search ............................................. 514/383

[56] References Cited

U.S. PATENT DOCUMENTS

| | | | |
|---|---|---|---|
| 5,246,954 | 9/1993 | Greiner et al. | 514/383 |
| 5,256,683 | 10/1993 | Hutt et al. | 514/383 |
| 5,290,791 | 3/1994 | Greiner et al. | 514/383 |
| 5,358,958 | 10/1994 | Greiner et al. | 514/383 |

FOREIGN PATENT DOCUMENTS

| | | |
|---|---|---|
| 652926 | 9/1994 | Australia . |
| 0378953 | 7/1990 | European Pat. Off. . |
| 0433780 | 6/1991 | European Pat. Off. . |

OTHER PUBLICATIONS

Smith, "The triazoles–a product manager's dream," Agrow Research Technology Supplement, Jun. 1994, pp. 18–19.

Cochard, "Les Fongicides: Moyens de Lutte Chimique," Seminaire de Formation, Maladies des Gazons, from A.T.E. Seminar Les Maladies des Gazons Programme, Dec. 6–7, 1994, Paris, France. Full English language–translation, Cochard, Fungicides: Means of Chemical Control, Training Seminar on Turf Diseases, from A.T.E. Seminar Turf Diseases Program Dec. 6–7, 1994, Paris, France, also provided herewith.

*Turf & Ornamental Reference for Plant Protection Products,* 4th edition, 1995, C&P Press, Inc., New York, pp. L73–L74.

*Primary Examiner*—Allen J. Robinson
*Attorney, Agent, or Firm*—Burns, Doane, Swecker & Mathis

[57] ABSTRACT

Method of controlling fungal diseases of turf, characterized in that an effective amount of 2-(4-chlorobenzylidene)-5,5-dimethyl-1-(1H-1,2,4-triazol-1-ylmethyl)-1-cyclopentanol, also called triticonazole, is applied to this turf, and a fungicidal composition, especially for carrying out this process.

16 Claims, No Drawings

METHOD OF TREATING TURF

The present invention relates to a method of treating turf by applying a triazole-based fungicidal composition. It also relates to this fungicidal composition, especially for carrying out this process.

Amongst the very large number of triazoles, some products are known which can be used for controlling fungal diseases of turf.

However, the fungicidal treatment of turf must, in the case of golf courses, comply with certain constraints. Indeed, it is highly desirable for the appearance and the green colour of the golf course not to be altered in any way by the fungicidal treatment, so that it offers a pleasant view to the user.

It is known that the triazoles have shortcomings which are linked to their selectivity, especially their insufficient selectivity on turf. Depending on the weather conditions, especially in the case of high temperatures, these shortcomings can lead to changes in colour and appearance of the turf, which become evident, for example, by the appearance of dark or very light patches, or even by burns of a typical, yellowish-brown appearance.

It is the aim of the present invention to avoid the shortcomings described hereinabove.

A further aim of the present invention is to propose a fungicidal treatment of turf which avoids any risk of changes in colour and appearance of a golf course.

A further aim of the present invention is to propose a fungicidal treatment for turf of golf courses which does not lead to any phytotoxicity to the turf.

It has now been found that these aims can be achieved fully or to some extent with the aid of the treatment method according to the invention described hereinbelow.

The present invention therefore relates, first and foremost, to a method of controlling fungal diseases of turf, characterized in that an effective amount of 2-(4-chlorobenzylidene)-5,5-dimethyl-1-(1H-1,2,4-triazol-1-ylmethyl)-1-cyclopentanol, also called triticonazole, is applied to this turf. Triticonazole is disclosed as a fungicide in European Patent Application EP 0378953 and, surprisingly, shows an improved selectivity when applied to turf.

By turf there is understood a group of annual or perennial Gramineae which cover a surface area of ground subject to regular maintenance and which belong, especially, to one or more of the genera Poa, Agrostis, Festuca, Phleum, Lolium, Zoysia.

The fungal diseases of turf which the method according to the invention makes it possible to control are caused by one or more phytopathogenic fungi belonging to the genera Sclerotinia (also called Lanzia or Moellerodiscus), Puccinia, Laetisaria, Fusarium, Gaeumannomyces (also called Ophiobolus), it also being possible for this phytopathogenic fungus, or these phytopathogenic fungi, to be associated with a fungus belonging to the genus Rhizoctonia.

The dose of triticonazole applied in practice can be varied within a wide range, depending on the climatic conditions and the modes of treatment. This dose amounts generally to between 100 and 1500 g/ha, preferably between 200 and 1000, even more preferably between 300 and 800, g/ha.

The triticonazole which is applied in the method according to the invention is part of a fungicidal composition which comprises, apart from this compound, an inert carrier which is suitable for agriculture and, if appropriate, a surfactant which is also suitable for agriculture.

The invention furthermore relates to such a composition for the treatment of turf.

The composition according to the invention usually contains between 0.5 and 95% of triticonazole.

By the term "carrier" in the present account, there is understood an organic or inorganic, natural or synthetic substance with which the triticonazole is combined to facilitate its application to turf. This carrier is therefore, in general, inert and must be suitable for agriculture, especially on the treated turf. The carrier can be solid (clays, natural or synthetic silicates, silica, resins, waxes, solid fertilizers and the like) or liquid (water, alcohols, ketones, petroleum fractions, aromatic or paraffinic hydrocarbons, chlorinated hydrocarbons, liquified gases and the like).

The surfactant can be an ionic or non-ionic emulsifier, dispersant or wetting agent. Examples which may be mentioned are, salts of polyacrylic acids, salts of lignosulphonic acids, salts of phenolsulphonic or naphthalenesulphonic acids, polycondensates of ethylene oxide with fatty alcohols or fatty acids or fatty amines, substituted phenols (especially alkylphenols or arylphenols), salts of sulphosuccinic acid esters, taurine derivatives (especially alkyltaurates), phosphoric esters of alcohols or polyoxyethylated phenols. The presence of at least one surfactant is frequently required since triticonazole and/or the inert carrier are not soluble in water and the vehicle for application is water.

This composition can also contain any other ingredients such as, for example, protective colloids, adhesives, thickeners, thixotropic agents, penetrants, stabilizers, sequestering agents, pigments, colourants, or polymers.

More generally, the composition according to the invention can be combined with all those solid or liquid additives which are conventionally used in formulation techniques.

The methods of application are well known to a person skilled in the art and can be used within the scope of the present invention without disadvantage.

Examples which may be mentioned are spraying or dusting.

In general, solid or liquid compositions may be mentioned amongst the compositions according to the present invention.

As solid forms of compositions, the following may be mentioned: powders for dusting or dispersing (with the compound, or triticonazole, content being able to range up to 100%) and granules, especially those obtained by extrusion, compacting, impregnation of a granulated carrier, or by granulation of a powder (the triticonazole content of these granules being between 1 and 80% in the last-mentioned cases).

The compositions can also be used in the form of a powder for dusting; thus, a composition can be used which comprises 50 g of triticonazole, 10 g of finely divided silica, 10 g of organic pigment and 970 g of talc; these components are mixed and ground and the mixture is applied by dusting.

As liquid forms of compositions, or forms intended to give liquid compositions on application, the following may be mentioned: flowables, wettable powders (or sprayable powder), pastes and dispersible granules.

The flowables, which can be applied by spraying, are prepared in such a way that a fluid stable product is obtained which does not form deposits, and they contain, as a rule, 10 to 75% of triticonazole, 0.5 to 15% of surfactants, 0.1 to 10% of thixotropic agents, 0 to 10% of suitable additives, such as pigments, colourants, antifoams, corrosion inhibitors, stabilizers, penetrants and adhesives, and, as carrier, water or an organic liquid in which triticonazole is sparingly soluble or insoluble: certain organic solid substances or mineral salts can be dissolved in the carrier to aid the prevention of sedimentation or as antifreeze agents for the water.

3

The wettable powders (or sprayable powder) are, as a rule, prepared in such a manner that they contain 20 to 95% of triticonazole, and they contain, as a rule, in addition to the solid carrier, 0 to 5% of a wetting agent, 3 to 10% of a dispersant, and, if required, 0 to 10% of one or more stabilizers and/or other additives, such as pigments, colourants, penetrants, adhesives, or anticaking agents, colourants and the like.

To obtain these sprayable powders, or wettable powders, the triticonazole is mixed intimately in suitable mixers with the additional substances, and the mixture is ground in mills or other suitable grinders. This gives sprayable powders whose wettability and suspensibility are advantageous; they can be suspended in water at any desired concentration, and these suspensions can be used very advantageously, in particular for application to turf.

Instead of wettable powders, pastes can be made. The conditions and modes of making and using these pastes resemble those of the wettable powders, or sprayable powders.

As a rule, dispersible granules are prepared by agglomerating in granulation systems which are suitable for compositions of the wettable powder type.

As has already been mentioned, aqueous dispersions, for example compositions obtained by diluting a wettable powder according to the invention with the aid of water, are encompassed within the general scope of the present invention.

Amongst the compositions, a person skilled in the art will select advantageously the composition, or compositions, which are suitable under the application conditions.

The examples which follow are given solely by way of illustrating the present invention and in no way whatsoever by way of limitation. In all these examples, triticonazole showed no symptom of phytotoxicity whatsoever, and, in particular, allowed the turf to retain a visually attractive green colour.

EXAMPLE 1

Field treatment of turf (Agrostis palustris) contaminated with *Sclerotinia homoeocarpa:*

An aqueous suspension of triticonazole is prepared using techniques well known to a person skilled in the art.

A quantity of a suspension which corresponds to a triticonazole dose shown in the table hereinbelow and expressed in g/ha is sprayed onto turf which has been artificially contaminated with *Sclerotinia homoeocarpa.*

This treatment is repeated twice at an interval of 1 treatment every 28 days.

23 days after the last treatment, the results are observed. To this end, the fraction B of the ground covered by turf, expressed as a percentage of the total surface area, which shows necroses, that is to say brown patches, which are typical of the disease caused by the phytopathogenic fungus, is estimated visually.

Equally, the fraction A of this ground which shows necroses which are typical of the disease caused by the phytopathogenic fungus is determined for a surface area of ground covered with turf which was also artificially contaminated with *Sclerotinia homoeocarpa* but did not receive any fungicidal treatment.

Then, the effectiveness E, expressed as a percentage, of the fungicidal treatment according to the invention is calculated using the formula:

$E=(A-B)/A$

4

The results of effectiveness are shown in the table which follows:

| Dose (in g/ha) | Effectiveness (in %) |
|---|---|
| 320 | 99 |
| 640 | 100 |

EXAMPLE 2

Field treatment of turf (Poa pratensis) contaminated with *Puccinia graminis:*

An aqueous suspension of triticonazole is prepared using techniques well known to a person skilled in the art.

A quantity of a suspension which corresponds to a triticonazole dose shown in the table hereinbelow and expressed in g/ha is sprayed onto the turf which has been naturally contaminated with *Puccinia graminis.*

29 days after the treatment, the results are observed, and the effectiveness of the treatment which has been carried out is determined as shown in Example 1.

The results of effectiveness are shown in the table which follows:

| Dose (in g/ha) | Effectiveness (in %) |
|---|---|
| 500 | 99.2 |
| 1000 | 99.6 |

What is claimed:

1. A method for controlling fungal disease in turf without substantial color damage, said method comprising applying to the turf an effective antifungal amount of triticonazole which does not cause substantial damage to the green color of the treated turf.

2. The method according to claim 1, wherein the turf is a group of annual or perennial Gramineae belonging to at least one of the genera Poa, Agrostis, Festuca, Phleum, Lolium, or Zoysia.

3. The method according to claim 1, wherein the fungal disease is caused by one or more phytopathogenic fungi belonging to the genera Sclerotinia, Puccinia, Laetisaria, Fusarium or Gaeumannomyces.

4. The method according to claim 3, wherein one or more of said phytopathogenic fungi are associated with a fungus of the genus Rhizoctonia.

5. The method according to claim 2, wherein the fungal disease is caused by one or more phytopathogenic fungi belonging to the genera Sclerotinia, Puccinia, Laetisaria, Fusarium or Gaeumannomyces.

6. The method according to claim 5, wherein one or more of said phytopathogenic fungi are associated with a fungus belonging to the genus Rhizoctonia.

7. The method according to claim 1, wherein triticonazole is applied in an amount between 100 and 1500 g/ha.

8. The method according to claim 7, wherein triticonazole is applied in an amount between 200 and 1000 g/ha.

9. The method according to claim 8, wherein triticonazole is applied in an amount between 300 and 800 g/ha.

10. The method according to claim 2, wherein triticonazole is applied in an amount between 100 and 1500 g/ha.

11. The method according to claim 10, wherein triticonazole is applied in an amount between 200 and 1000 g/ha.

12. The method according to claim 11, wherein triticonazole is applied in an amount between 300 and 800 g/ha.

13. The method according to claim 3, wherein triticonazole is applied in an amount between 100 and 1500 g/ha.

14. The method according to claim 13, wherein triticonazole is applied in an amount between 200 and 1000 g/ha.

15. The method according to claim 14, wherein triticonazole is applied in an amount of between 300 and 800 g/ha.

16. The method according to claim 1, wherein the turf is that of a golf course.

* * * * *